US010472371B2

(12) United States Patent
Zheng et al.

(10) Patent No.: US 10,472,371 B2
(45) Date of Patent: *Nov. 12, 2019

(54) COMPOSITIONS FOR ACTIVATING PYRUVATE KINASE

(71) Applicant: FORMA Therapeutics, Inc., Watertown, MA (US)

(72) Inventors: Xiaozhang Zheng, Lexington, MA (US); Neal Green, Newton, MA (US); Gary Gustafson, Ridgefield, CT (US); David R. Lancia, Jr., Boston, MA (US); Lorna Mitchell, West Beach (AU); Tatiana Shelekhin, Ridgefield, CT (US)

(73) Assignee: FORMA THERAPEUTICS, INC., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/245,654

(22) Filed: Jan. 11, 2019

(65) Prior Publication Data

US 2019/0218221 A1 Jul. 18, 2019

Related U.S. Application Data

(63) Continuation of application No. 15/926,236, filed on Mar. 20, 2018, now Pat. No. 10,208,052.

(60) Provisional application No. 62/473,751, filed on Mar. 20, 2017.

(51) Int. Cl.
*C07D 487/04* (2006.01)
*C07D 519/00* (2006.01)
*A61P 7/00* (2006.01)
*A61K 9/00* (2006.01)
*A61K 31/407* (2006.01)

(52) U.S. Cl.
CPC .......... *C07D 487/04* (2013.01); *A61K 9/0053* (2013.01); *A61K 31/407* (2013.01); *A61P 7/00* (2018.01); *C07D 519/00* (2013.01)

(58) Field of Classification Search
None
See application file for complete search history.

(56) References Cited

U.S. PATENT DOCUMENTS

| | | | |
|---|---|---|---|
| 5,030,631 A | 7/1991 | Bauer | |
| 5,089,621 A | 2/1992 | Kim et al. | |
| 5,091,384 A | 2/1992 | Kim et al. | |
| 5,480,899 A | 1/1996 | Yano et al. | |
| 5,962,703 A | 10/1999 | Moszner et al. | |
| 6,214,879 B1 | 4/2001 | Abraham et al. | |
| 6,534,501 B2 | 3/2003 | Abraham et al. | |
| 7,875,603 B2 | 1/2011 | Rathinavelu et al. | |
| 8,501,953 B2 | 8/2013 | Salituro et al. | |
| 8,552,050 B2 | 10/2013 | Cantley et al. | |
| 8,692,001 B2 | 4/2014 | Becker et al. | |
| 8,742,119 B2 | 6/2014 | Salituro et al. | |
| 8,785,450 B2 | 7/2014 | Salituro et al. | |
| 8,841,305 B2 | 9/2014 | Thomas et al. | |
| 8,877,791 B2 | 11/2014 | Cantley et al. | |
| 8,889,667 B2 | 11/2014 | Salituro et al. | |
| 9,108,921 B2 | 8/2015 | Cianchetta et al. | |
| 9,181,231 B2 | 11/2015 | Su | |
| 9,221,792 B2 | 12/2015 | Salituro et al. | |
| 9,328,077 B2 | 5/2016 | Salituro et al. | |
| 9,394,257 B2 | 7/2016 | Ho et al. | |
| 9,458,132 B2 | 10/2016 | Cianchetta et al. | |
| 9,708,267 B2 | 7/2017 | Boxer et al. | |
| 9,744,145 B1 | 8/2017 | Liu et al. | |
| 10,208,052 B1 * | 2/2019 | Zheng | A61K 31/407 |
| 2006/0074121 A1 | 4/2006 | Chen et al. | |
| 2007/0270433 A1 | 11/2007 | Brinkman et al. | |
| 2008/0184495 A1 | 8/2008 | Brun et al. | |
| 2010/0120863 A1 | 5/2010 | Biftu et al. | |
| 2010/0144594 A1 | 6/2010 | Zoller et al. | |
| 2010/0216774 A1 | 8/2010 | Bender et al. | |
| 2010/0324030 A1 | 12/2010 | Dale et al. | |
| 2013/0116430 A1 | 5/2013 | Fujiwara et al. | |
| 2013/0155489 A1 | 6/2013 | Kato et al. | |
| 2015/0246025 A1 | 9/2015 | Desai et al. | |
| 2016/0200681 A1 | 7/2016 | Yu et al. | |
| 2017/0121338 A1 | 5/2017 | Zhang et al. | |
| 2017/0217964 A1 | 8/2017 | Li | |

FOREIGN PATENT DOCUMENTS

| | | | |
|---|---|---|---|
| CN | 101812063 A | 8/2010 | |
| CN | 102206217 A | 10/2011 | |
| CN | 102952139 A | 3/2013 | |
| CN | 103570722 A | 2/2014 | |
| CN | 105037367 A | 11/2015 | |
| CN | 105085528 A | 11/2015 | |
| CN | 105153119 A | 12/2015 | |
| CN | 105254628 A | 1/2016 | |

(Continued)

OTHER PUBLICATIONS

Aiuti, A. et al, Progress and prospects: gene therapy clinical trials (part 2), Gene Ther, 14(22): 1555-1563 (2007).

Alves-Filho, J.C. & Palsson-Mcdermott, E.M., Pyruvate Kinase M2: A Potential Target for Regulating Inflammation, Frontiers in Immunology, 7(145): Article 145 (2016).

Ambrus, J. et al., Studies on the vasoocclusive crisis of sickle cell disease. III. In vitro and in vivo effect of the pyrimido-pyrimidine derivative, RA-233: studies on its mechanism of action, J Med, 18(3-4):165-198 (1987).

Amer, J. et al., Red blood cells, platelets and polymorphonuclear neutrophils of patients with sickle cell disease exhibit oxidative stress that can be ameliorated by antioxidants, British Journal of Haematology, 132(1):108-113 (2006).

(Continued)

*Primary Examiner* — Brian J Davis
(74) *Attorney, Agent, or Firm* — Brinks Gilson & Lione

(57) ABSTRACT

Compositions for the activation of PKR are provided, as well as therapeutic administration of the compositions for the treatment of pyruvate kinase-related medical conditions, such as pyruvate kinase deficiency (PKD).

3 Claims, No Drawings

(56) References Cited

FOREIGN PATENT DOCUMENTS

| | | |
|---|---|---|
| CN | 105294694 A | 2/2016 |
| CN | 105348286 A | 2/2016 |
| EP | 424851 A1 | 5/1991 |
| EP | 1952800 A2 | 8/2008 |
| IN | 2013MU01809 | 3/2015 |
| JP | 2004175674 A | 6/2004 |
| JP | 2007246885 A | 9/2007 |
| JP | 2007328090 A | 12/2007 |
| JP | 2008031064 A | 2/2008 |
| JP | 2008063256 A | 3/2008 |
| JP | 2009149707 A | 7/2009 |
| JP | 2010192782 A | 9/2010 |
| JP | 2011246649 A | 12/2011 |
| JP | 2012188474 A | 10/2012 |
| JP | 2012188475 A | 10/2012 |
| KR | 20110096442 A | 8/2011 |
| LB | 11379 | 7/2018 |
| WO | WO-9322298 A1 | 11/1993 |
| WO | WO-9519353 A1 | 7/1995 |
| WO | WO-9947489 A1 | 9/1999 |
| WO | WO-9948490 A1 | 9/1999 |
| WO | WO-2002060902 A1 | 8/2002 |
| WO | WO-2002076989 A1 | 10/2002 |
| WO | WO-2003067332 A2 | 8/2003 |
| WO | WO-2004013144 A1 | 2/2004 |
| WO | WO-2004014374 A1 | 2/2004 |
| WO | WO-2004080457 A1 | 9/2004 |
| WO | WO-2004089947 A2 | 10/2004 |
| WO | WO-2005084667 A1 | 9/2005 |
| WO | WO-2005103015 A1 | 11/2005 |
| WO | WO-2006018279 A2 | 2/2006 |
| WO | WO-2006018280 A2 | 2/2006 |
| WO | WO-2006/084030 A2 | 8/2006 |
| WO | WO-2006123121 A1 | 11/2006 |
| WO | WO-2007007069 A1 | 1/2007 |
| WO | WO-2007027734 A2 | 3/2007 |
| WO | WO-2007042325 A1 | 4/2007 |
| WO | WO-2008/005937 A2 | 1/2008 |
| WO | WO-2008094203 A2 | 8/2008 |
| WO | WO-2008/115719 A1 | 9/2008 |
| WO | WO-2008120003 A1 | 10/2008 |
| WO | WO-2008135141 A1 | 11/2008 |
| WO | WO-2009001126 A1 | 12/2008 |
| WO | WO-2009077527 A1 | 6/2009 |
| WO | WO-2009136889 A1 | 11/2009 |
| WO | WO-2009153554 A1 | 12/2009 |
| WO | WO-2010002802 A1 | 1/2010 |
| WO | WO-2010021717 A2 | 2/2010 |
| WO | WO-2010028761 A1 | 3/2010 |
| WO | WO-2010092181 A1 | 8/2010 |
| WO | WO-2010115688 A1 | 10/2010 |
| WO | WO-2010132599 A1 | 11/2010 |
| WO | WO-2010135524 A1 | 11/2010 |
| WO | WO-2011025690 A1 | 3/2011 |
| WO | WO-2011037793 A1 | 3/2011 |
| WO | WO-2011060321 A1 | 5/2011 |
| WO | WO-2011103256 A1 | 8/2011 |
| WO | WO-2011116282 A2 | 9/2011 |
| WO | WO-2011146358 A1 | 11/2011 |
| WO | WO-2012002577 A1 | 1/2012 |
| WO | WO-2012068096 A2 | 5/2012 |
| WO | WO-2012071519 A1 | 5/2012 |
| WO | WO-2012/151450 A1 | 11/2012 |
| WO | WO-2013003249 A1 | 1/2013 |
| WO | WO-2013003250 A1 | 1/2013 |
| WO | WO-2013021054 A1 | 2/2013 |
| WO | WO-2013038390 A1 | 3/2013 |
| WO | WO-2013126856 A1 | 8/2013 |
| WO | WO-2013127266 A1 | 9/2013 |
| WO | WO-2013155223 A1 | 10/2013 |
| WO | WO-2014018355 A1 | 1/2014 |
| WO | WO-2014023814 A1 | 2/2014 |
| WO | WO-2014048865 A1 | 4/2014 |
| WO | WO-2014061031 A1 | 4/2014 |
| WO | WO-2014102817 A1 | 7/2014 |
| WO | WO-2014/139144 A1 | 9/2014 |
| WO | WO-2014/144715 A1 | 9/2014 |
| WO | WO-2014139978 A1 | 9/2014 |
| WO | WO-2014152588 A1 | 9/2014 |
| WO | WO-2015030514 A1 | 3/2015 |
| WO | WO-2015042397 A1 | 3/2015 |
| WO | WO-2015051230 A1 | 4/2015 |
| WO | WO-2015130915 A1 | 9/2015 |
| WO | WO-2015144605 A1 | 10/2015 |
| WO | WO-2015172732 A1 | 11/2015 |
| WO | WO-2015192701 A1 | 12/2015 |
| WO | WO-2016005576 A1 | 1/2016 |
| WO | WO-2016005577 A1 | 1/2016 |
| WO | WO-2016014324 A1 | 1/2016 |
| WO | WO-2016/044629 | 3/2016 |
| WO | WO-2016044604 A1 | 3/2016 |
| WO | WO-2016046837 A1 | 3/2016 |
| WO | WO-2016181408 A2 | 11/2016 |
| WO | WO-2016/201227 A1 | 12/2016 |
| WO | WO-2017050791 A1 | 3/2017 |
| WO | WO-2017050792 A1 | 3/2017 |
| WO | WO-2017214002 A1 | 12/2017 |
| WO | WO-2018109277 A1 | 6/2018 |
| WO | WO-2018/175474 A1 | 9/2018 |

OTHER PUBLICATIONS

Banerjee, T. and Kuypers F.A., Reactive oxygen species and phosphatidylserine externalization in murine sickle red cells, British Journal of Haematology, 124:391-402 (2004).

Beutler, E. and Gelbart, T., Estimating the prevalence of pyruvate kinase deficiency from the gene frequency in the general white population, Blood, 95(11): 3585-3588 (2000).

Bianchi, P. and Zanella, A., Hematologically important mutations: red cell pyruvate kinase (Third update), Blood Cells Mol Dis., 26(1): 47-53 (2000).

Boxer, M.B. et al., Evaluation of Substituted $N,N'$-Diarylsulfonamides as Activators of the Tumor Cell Specific M2 Isoform of Pyruvate Kinase, J. Med. Chem., 53: 1048-1055 (2010).

Cabrales, P. et al., A look inside the mechanistic black box: Are red blood cells the critical effectors of RRx-001 cytotoxicity?, Med Oncol., 33(7):63 (2016).

Castilhos, L. et al., Altered E-NTPDase/E-ADA activities and CD39 expression in platelets of sickle cell anemia patients, Biomed Pharmacother., 79:241-246 (2016).

Castilhos, L. et al., Increased oxidative stress alters nucleosides metabolite levels in sickle cell anemia, Redox Rep., 22(6):451-459 (2017).

Castro, O., Viability and function of stored sickle erythrocytes, Transfusion, 20(6):695-703 (1980).

Cazzola, M., Pyruvate kinase deficiency, Haematologica, 90(1): 1-2 (2005).

Charache, S. et al., Effect of 2,3-Diphosphateglycerate on oxygen affinity of blood in sickle cell anemia, Journal of Clinical Investigation, 49(4):806-812 (1970).

De Furia, F. et al., The effects of cyanate in vitro on red blood cell metabolism and function in sickle cell anemia, J Clin Invest., 51(3):566-574 (1972).

De Jong, K. and Kuypers, F., Sulphydryl modifications alter scramblase activity in murine sickle cell disease, British Journal of Haematology, 133(4):427-432 (2006).

Diez, A. et al., Life-threatening nonspherocytic hemolytic anemia in a patient with a null mutation in the PKLR gene and no compensatory PKM gene expression, Blood, 106:1851 (2005).

Estepp, J.H. et al., A clinically meaningful fetal hemoglobin threshold for children with sickle cell anemia during hydroxyurea therapy, Am J Hematol., 92:1333-1339 (2017).

Gizi, A. et al., Assessment of oxidative stress in patients with sickle cell disease: The glutathione system and the oxidant-antioxidant status, Blood Cells Mol Dis., 46(3):220-225 (2011).

Gladwin, M., Adenosine recepter crossroads in sickle cell disease, Nature Medicine, 17(1):38-40, (2011).

(56) References Cited

OTHER PUBLICATIONS

Glombitza, S. et al., Adenosine causes cAMP-dependent activation of chick embryo red cell carbonic anhydrase and 2,3-DPG synthesis, American Journal of Physiology, 271(4):973-81 (1996).
Hierso, R. et al., Effects of oxidative stress on red blood cell rheology in sickle cell patients, British Journal of Haematology, 166(4):601-606 (2014).
International Search Report for PCT/US2018/023405, 6 pages (dated Jun. 5, 2018).
Jendralla, H. et al., Synthesis of 1,2,3,4,5,6-Hexahydropyrrolo[3,4-c]pyrrole dihydrobromide and 1,2,3,5-Tetrahydro-2-[(4-Methyl-Phenyl)Sulfonyl]Pyrrolo[3,4-c]Pyrrole, Heterocycles, 41(6): 1291-1298 (1995).
Jin, Y. et al., Effects of gamma irradiation on red cells from donors with sickle cell trait, Transfusion, 37(8):804-808 (1997).
Kalai, T. et al., Synthesis of Pyrroline Nitroxide Annulated Carbocycles and Heterocycles, Synthesis No. 6, pp. 831-837 (2000).
Kharalkar, S.S. et al., Identification of Novel Allosteric Regulators of Human-Erythrocyte Pyruvate Kinase, Chemistry & Biodiversity, vol. 4, pp. 2603-2617 (Feb. 2007).
Kodama, K. et al., Solvent-induced dual chirality switching in the optical resolution of tropic acid via diastereomeric salt formation with (1R,2S)-2-amino-1,2-diphenylethanol, Tetrahedron 70:7923-7928 (2014).
Kuehl, G. et al., In vitro interactions of 51Cr in human red blood cells and hemolysates, Vox Sang., 40(4):260-272 (1981).
Kurita, R. et al., Establishment of Immortalized Human Erythroid Progenitor Cell Lines Able to Produce Enucleated Red Blood Cells, PLOS One, vol. 8, Iss.3, pp. 1-15 (Mar. 2013).
Le Quesne, P.W. et al., One-Step Preparation of Tetrakis(bromomethyl)ethylene from Pinacolyl Alcohol, J. Org. Chem., 40(1): 142-143 (1975).
Lochmatter, C. et al., Integrative phosphoproteomics links IL-23R signalling with metabolic adaption in lymphocytes, Scientific Reports, 6:24491 (2016).
Lockwood, S. et al., Endothelium-derived nitric oxide production is increased by ATP released from red blood cells incubated with hydroxyurea, Nitric Oxide, 38:1-7 (2014).
Macdonald, Rosemary, Red cell 2,3-diphosphoglycerate and oxygen affinity, Anaesthesia, vol. 32, pp. 544-553, (1977).
Meza, N.W. et al, In vitro and in vivo expression of human erythrocyte pyruvate kinase in erythroid cells: a gene therapy approach, Hum Gene Ther, 18(6):502-514 (2007).
Middelkoop, E. et al., Studies on sickled erythrocytes provide evidence that the asymmetric distribution of phosphatidylserine in the red cell membrane is maintained by both ATP-dependent translocation and interaction with membrane skeletal proteins, Biochimica et Biophysica Acta, 937:281-288 (1988).
Miwa, S. and Fujii, H., Molecular basis of erythroenzymopathies associated with hereditary hemolytic anemia: tabulation of mutant enzymes, Am J Hematol., 51(2): 122-132 (1996).
Muzyamba, M. and Gibson, J., Effect of 1-chloro-2,4-dinitrobenzene on K+ transport in normal and sickle human red blood cells, Journal of Physiology, 547(3):903-911 (2003).
Ould Amar, A.K. et al., Assessment of qualitative functional parameters of stored red blood cells from donors with sickle cell trait (AS) or with heterozygote (AC) status, Transfus Clin Biol., 3(4):225-233 (1996).
Palsson-Mcdermott, EM et al., Pyruvate kinase M2 regulates Hif-1a activity and IL-1β induction and is a critical determinant of the Warburg Effect in LPS-activated macrophages, Cell Metabolism, 21:65-80 (2015).

Poillon W., & Kim, B., 2,3-Diphosphoglycerate and intracellular pH as interdependent determinants of the physiologic solubility of deoxyhemoglobin S, Blood, 76:1028-1036 (1990).
Poillon, W. et al., Antisickling effects of 2,3-Diphosphoglycerate depletion, Blood, 85(11):3289-3296 (1995).
Poillon, W. et al., The Effect of 2,3-Diphosphoglycerate on the Solubility of Deoxyhemoglobin $S^1$, Archives of Biochemistry and Biophysics, vol. 249, No. 2, pp. 301-305, (Sep. 1986).
Poillon, W. et al., Intracellular hemoglobin S polymerization and the clinical severity of sickle cell anemia, Blood, 91:1777-1783 (1998).
Ramdani, G. and Langsley, G., ATP, an Extracellular Signaling Molecule in Red Blood Cells: A Messenger for Malaria?, Biomed Journal, 37(5):284-292 (2014).
Raththagala, M. et al., Hydroxyurea stimulates the release of ATP from rabbit erythrocytes through an increase in calcium and nitric oxide production, European Journal of Pharmacology, 645(1-3):32-38 (2010).
Rosa, M. et al., Allosteric properties of hemoglobin and the plasma membrane of the erythrocyte: New insights in gas transport and metabolic modulation, Life, 60(2):87-93 (2008).
Schwartz, R. et al., Two distinct pathways mediate the formation of intermediate density cells and hyperdense cells from normal density sickle red blood cells, Blood, 92(12):4844-4855 (1998).
Sega, M. et al., Fluorescence assay of the interaction between hemoglobin and the cytoplasmic domain of erythrocyte membrane band 3, Blood Cells Mol Dis., 55(3):266-271 (2015).
Soupene, E. and Kuypers, F., Identification of an erythroid ATP-dependent aminophospholipid transporter, British Journal of Haematology, 133(4):436-438 (2006).
Stasiuk, M. et al., Transformations of erythrocytes shape and its regulation, Postepy Biochem., 55(4):425-33 (2009). English Abstract.
Takenaka, M. et al, Isolation and characterization of the human pyruvate kinase M gene, Eur J Biochem, 198(1):101-106 (1991).
Tanphaichitr, V.S. et al, Successful bone marrow transplantation in a child with red blood cell pyruvate kinase deficiency, Bone Marrow Transplant, 26(6):689-690 (2000).
Tripathi, Ashutoshi and Safo, Martin K., In Silico-Screening Approaches for Lead Generation: Identification of Novel Allosteric Modulators of Human-Erythrocyte Pyruvate Kinase, Allostery: Methods and Protocols, Methods in Molecular Biology, Chpt. 19, vol. 796, pp. 351-367 (2012).
Van Zweiten, R. et al., Inborn defects in the antioxidant systems of human red blood cells, Free Radio Biol Med., 67:377-386 (2014).
Verma, S.K. et al., Imidazole-Catalyzed Monoacylation of Symmetrical Diamines, Organic Letters, 12(19): 4232-4235 (201).
Wagner, G. et al., Red cell vesiculation—a common membrane physiologic event, J Lab Clin., 108(4):315-324 (1986).
Wang, H. et al., JMJD5 regulates PKM2 nuclear translocation and reprograms HIF-1a-mediated glucose metabolism, PNAS, 111(1):279-284 (2014).
Weatherall, D., The inherited diseases of hemoglobin are an emerging global health burden, Blood, 115(22):4331-43336 (2010).
Willcocks, J. et al., Simultaneous determination of low free Mg2+ and pH in human sickle cells using P NMR spectroscopy, The Journal of Biological Chemistry, 277(51):49911-49920 (2002).
Wright, S.W. et al., A Convenient Preparation of Heteroaryl Sulfonamides and Sulfonyl Fluorides from Heteroaryl Thiols, J. Org. Chem., 71: 1080-1084 (2006).
Zhang, Y & Xia, Y., Adenosine signaling in normal and sickle erythrocytes and beyond, Microbes Infect., 14(10) (2012).
Zhang, Y. et al., Detrimental effects of adenosine signaling in sickle cell disease, Nature Medicine, 17(1):79-87 (2011).

* cited by examiner

COMPOSITIONS FOR ACTIVATING PYRUVATE KINASE

RELATED PATENT APPLICATIONS

The present patent application is a continuation of U.S. patent application Ser. No. 15/926,236, now U.S. Pat. No. 10,208,052, filed on Mar. 20, 2018, which application claims priority to U.S. Provisional Patent Application No. 62/473,751, filed on Mar. 20, 2017, the entire contents of all of which are hereby incorporated by reference.

TECHNICAL FIELD

This disclosure relates to novel chemical compositions for activating the pyruvate kinase enzyme, useful in the treatment of pyruvate kinase-related medical conditions (e.g., pyruvate kinase deficiency).

BACKGROUND

Pyruvate Kinase (PK) is an enzyme involved in glycolysis (the conversion of glucose into pyruvate), and is critical for the survival of the cell. PK converts phosphoenolpyruvate (PEP) and adenosine diphosphate (ADP) to pyruvate and adenosine triphosphate (ATP), respectively, which is the final step in glycolysis. PKR is one of several tissue-specific isoforms (e.g., PKR, PKL, PKM1, and PKM2) of pyruvate kinase that is present in red blood cells (RBCs). Glycolysis is the only pathway available for RBCs to maintain the production of adenosine-5'-triphosphate, or ATP, which is a form of chemical energy within cells. Accordingly, PK deficiency can result in a shortened life span for RBCs and is the most common form of non-spherocytic hemolytic anemia in humans.

PK deficiency (PKD) is a rare autosomal recessive genetic disorder that can result in severe hemolytic anemia, jaundice, and lifelong conditions associated with chronic anemia, as well as secondary complications due to inherited mutations in the pyruvate kinase enzyme within RBCs. Individuals with the PK deficiency produce PKR enzyme at only a fraction of the normal level of activity (generally <50%). There are many different possible mutant combinations, classified as either a missense mutation (causing a single amino acid change in the protein), generally resulting in some level of functional protein in the RBCs, or a non-missense mutation (any mutation other than a missense mutation), generally resulting in little functional protein in the RBCs. It is estimated that 58 percent of patients with PK deficiency have two missense mutations, 27 percent have one missense and one non-missense mutation, and 15 percent have two non-missense mutations.

There remains a need for novel compounds that activate PKR for the treatment of PK deficiency and other medical conditions that can therapeutically benefit from compounds that activate PKR.

SUMMARY

Compositions disclosed herein include compounds useful for activating PKR. The invention is based in part on the discovery of the chemical compound 1 as a PKR Activator Compound, defined herein as a compound that provides an $AC_{50}$ value of less than 1 μM using the Luminescence Assay described below:

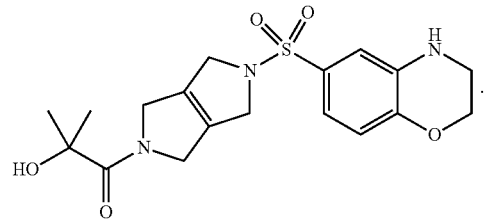

The discovery includes the use of 1-(5-(((3,4-Dihydro-2H-benzo[b][1,4]oxazin-6-yl)sulfonyl)-3,4,5,6-tetrahydropyrrolo[3,4-c]pyrrol-2(1H)-yl)-2-hydroxy-2-methylpropan-1-one, and pharmaceutically acceptable salts thereof, in pharmaceutical preparations for the treatment of patients diagnosed with a pyruvate kinase-related condition, such as pyruvate kinase deficiency. The compositions comprising compound 1 and pharmaceutically acceptable salts thereof can be obtained by certain processes also provided herein.

DETAILED DESCRIPTION

Compositions comprising compound 1 can be prepared as shown in the scheme below:

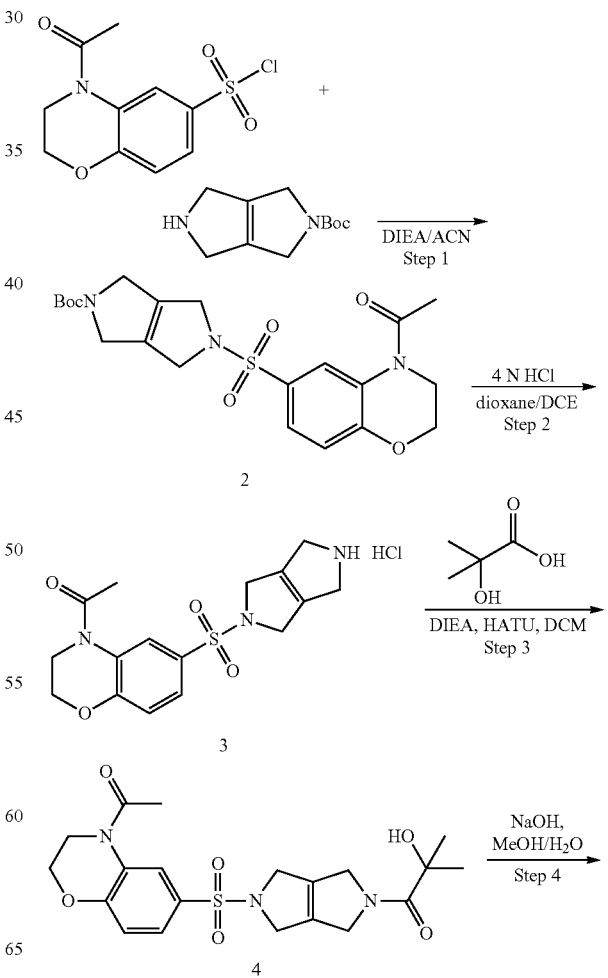

-continued

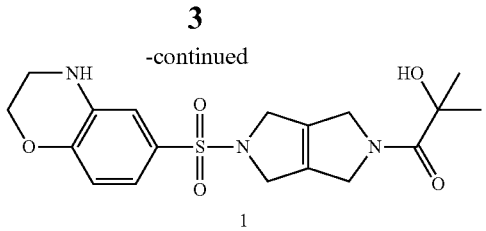

1

Step 1. tert-butyl 5-((4-acetyl-3,4-dihydro-2H-benzo[b][1,4]oxazin-6-yl)sulfonyl)-3,4,5,6-tetrahydropyrrolo[3,4-c]pyrrole-2(1H)-carboxylate (2)

To a solution of tert-butyl 3,4,5,6-tetrahydropyrrolo[3,4-c]pyrrole-2(1H)-carboxylate (0.7 g, 3.33 mmol, 1.00 equiv) in acetonitrile (20 mL) and DIEA (1.7 mL, 9.76 mmol, 2.93 equiv) is added 4-acetyl-3,4-dihydro-2H-benzo[b][1,4]oxazine-6-sulfonyl chloride (0.96 g, 3.50 mmol, 1.05 equiv) in 1,4 dioxane (17 mL). The resulting mixture is stirred at RT overnight. The reaction mixture is worked up with saturated ammonium chloride solution and EtOAc. The combined organics are washed with brine, dried over $Na_2SO_4$, filtered, and concentrated under reduced pressure to provide tert-butyl 5-((4-acetyl-3,4-dihydro-2H-benzo[b][1,4]oxazin-6-yl)sulfonyl)-3,4,5,6-tetrahydropyrrolo[3,4-c]pyrrole-2(1H)-carboxylate (2) (1.5 g, 3.33 mmol, 100% yield).

Step 2. 1-(6-((3,4,5,6-tetrahydropyrrolo[3,4-c]pyrrol-2(1H)-yl)sulfonyl)-2,3-dihydro-4H-benzo[b][1,4]oxazin-4-yl)ethan-1-one hydrochloride (3)

Tert-butyl 5-((4-acetyl-3,4-dihydro-2H-benzo[b][1,4]oxazin-6-yl)sulfonyl)-3,4,5,6-tetrahydropyrrolo[3,4-c]pyrrole-2(1H)-carboxylate (2) (1.5 g, 3.33 mmol, 1.00 equiv) is dissolved in a mixture of MeOH (30 mL), DCE (10 mL) and 4 M HCl in 1,4-dioxane (5 mL). The reaction is heated at 50° C. for 2 h. The solvents are evaporated under reduced pressure and the reaction mixture is azeotropically dried with toluene and dried further under vacuum overnight to provide 1-(6-((3,4,5,6-tetrahydropyrrolo[3,4-c]pyrrol-2(1H)-yl)sulfonyl)-2,3-dihydro-4H-benzo[b][1,4]oxazin-4-yl)ethan-1-one hydrochloride (3) (1.21 g, 3.13 mmol, 94% yield, over two steps). LCMS: m/z=350 [M+H]$^+$.

Step 3. 1-(5-((4-acetyl-3,4-dihydro-2H-benzo[b][1,4]oxazin-6-yl)sulfonyl)-3,4,5,6-tetrahydropyrrolo[3,4-c]pyrrol-2(1H)-yl)-2-hydroxy-2-methylpropan-1-one (4)

Into an 8-mL vial purged and maintained with an inert atmosphere of nitrogen is added 2-hydroxy-2-methylpropanoic acid (0.050 g, 0.48 mmol, 1.20 equiv), DIEA (154.8 mg, 1.20 mmol, 3.00 equiv), 1-(6-((3,4,5,6-tetrahydropyrrolo[3,4-c]pyrrol-2(1H)-yl)sulfonyl)-2,3-dihydro-4H-benzo[b][1,4]oxazin-4-yl)ethan-1-one hydrochloride (3) (0.154 g, 0.40 mmol, 1.00 equiv), HATU (0.167 g, 0.44 mmol, 1.10 equiv), and dichloromethane (4 ml). The solution is stirred for 4 h at room temperature, then concentrated under vacuum. The crude product is purified by prep-TLC to provide 1-(5-((4-acetyl-3,4-dihydro-2H-benzo[b][1,4]oxazin-6-yl)sulfonyl)-3,4,5,6-tetrahydropyrrolo[3,4-c]pyrrol-2(1H)-yl)-2-hydroxy-2-methylpropan-1-one (4).

Step 4. 1-(5-((3,4-dihydro-2H-benzo[b][1,4]oxazin-6-yl)sulfonyl)-3,4,5,6-tetrahydropyrrolo[3,4-c]pyrrol-2(1H)-yl)-2-hydroxy-2-methylpropan-1-one (1)

Into an 8-mL vial is placed 1-(5-((4-acetyl-3,4-dihydro-2H-benzo[b][1,4]oxazin-6-yl)sulfonyl)-3,4,5,6-tetrahydropyrrolo[3,4-c]pyrrol-2(1H)-yl)-2-hydroxy-2-methylpropan-1-one (4) (0.087 g, 0.20 mmol, 1.00 equiv) and a solution of sodium hydroxide (0.032 g, 0.80 mmol, 4.00 equiv) in methanol (2 ml) and water (0.5 ml). The solution is stirred for 4 h at room temperature, then the pH is adjusted to 9 with hydrochloric acid (2 mol/L). The mixture is concentrated under vacuum. The residue is purified by silica gel column chromatography. The crude product is further purified by Prep-HPLC to provide 1-(5-((3,4-dihydro-2H-benzo[b][1,4]oxazin-6-yl)sulfonyl)-3,4,5,6-tetrahydropyrrolo[3,4-c]pyrrol-2(1H)-yl)-2-hydroxy-2-methylpropan-1-one (1). LCMS m/z: 394.

The ability of compound 1 to activate PKR was determined using the following Luminescence Assay. The effect of phosphorylation of adenosine-5'-diphosphate (ADP) by PKR (wild type) is determined by the Kinase Glo Plus Assay (Promega) in the presence or absence of FBP [D-Fructose-1,6-diphosphate; BOC Sciences, CAS: 81028-91-3] as follows. Unless otherwise indicated, all reagents are purchased from Sigma-Aldrich. All reagents are prepared in buffer containing 50 mM Tris-HCl, 100 mM KCl, 5 mM $MgCl_2$, and 0.01% Triton X100, 0.03% BSA, and 1 mM DTT. Enzyme and PEP [Phospho(enol) pyruvic acid] are added at 2× to all wells of an assay-ready plate containing serial dilutions of test compounds or DMSO vehicle. Final enzyme concentrations for PKR(wt), PKR(R510Q), and PKR(G332S) are 0.8 nM, 0.8 nM, and 10 nM respectively. Final PEP concentration is 100 µM. The Enzyme/PEP mixture is incubated with compounds for 30 minutes at RT before the assay is initiated with the addition of 2×ADP [Adenosine-5'-diphosphate] and KinaseGloPlus. Final concentration of ADP is 100 µM. Final concentration of KinaseGloPlus is 12.5%. For assays containing FBP, that reagent is added at 30 µM upon reaction initiation. Reactions are allowed to progress for 45 minutes at RT until luminescence is recorded by the BMG PHERAstar FS Multilabel Reader. The compound is tested in triplicate at concentrations ranging from 42.5 µM to 2.2 nM in 0.83% DMSO. An $AC_{50}$ measurement for compound 1 of between 0.1 and 1.0 µM for the G332S PKR mutant, and between 0.1 and 1.0 µM for the PKR wild type enzyme was obtained by the standard four parameter fit algorithm of ActivityBase XE Runner (max, min, slope and $AC_{50}$). The $AC_{50}$ value for a compound is the concentration (µM) at which the activity along the four parameter logistic curve fit is halfway between minimum and maximum activity.

Compounds and compositions described herein are activators of wild type PKR and certain PKR mutants having lower activities compared to the wild type. Such mutations in PKR can affect enzyme activity (catalytic efficiency), regulatory properties and/or thermostability of the enzyme. One example of a PKR mutation is G332S. Methods of treatment (e.g., by activating wild type PKR) can comprise administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof and a pharmaceutically acceptable carrier. The pharmaceutical compositions may be orally administered in any orally acceptable dosage form. In some embodiments, to increase the lifetime of red blood cells, a compound, composition or pharmaceutical composition described herein is added directly to whole blood or packed cells extracorporeally or provided to the subject (e.g., the patient) directly. The compositions described herein can modulate (e.g., activate) PKR. Accordingly, a patient and/or subject can be selected for treatment using a compound described herein by first evaluating the patient and/or subject to determine whether the subject is in need of modulation (e.g., activation) of PKR, and if the subject is determined to be in need of modulation of PKR, then administering to the subject a composition described herein.

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description and drawings are by way of example to illustrate the discoveries provided herein.

We claim:

1. A composition comprising compound 2:

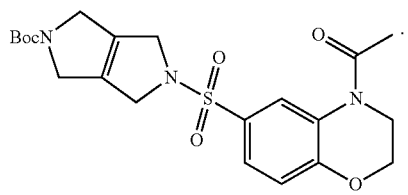

2

2. A composition comprising compound 3:

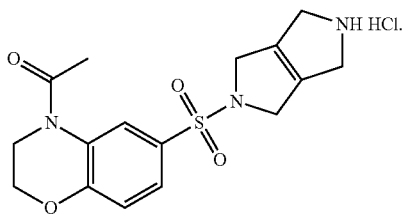

3

3. A composition comprising compound 4:

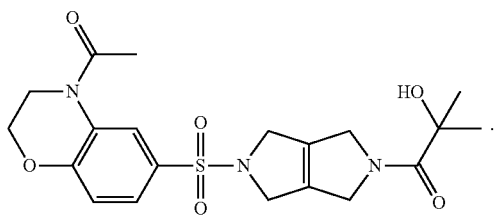

4

* * * * *